United States Patent [19]

Leonard

[11] 4,061,470

[45] Dec. 6, 1977

[54] BLOOD OXYGENATOR UTILIZING A REMOVABLE MEMBRANE OXYGENATOR UNIT

[75] Inventor: Ronald J. Leonard, Elk Grove Village, Ill.

[73] Assignee: Baxter Travenol Laboratories, Inc., Deerfield, Ill.

[21] Appl. No.: 735,863

[22] Filed: Oct. 27, 1976

Related U.S. Application Data

[60] Continuation of Ser. No. 622,184, Oct. 14, 1975, abandoned, which is a division of Ser. No. 435,143, Jan. 14, 1974, Pat. No. 3,929,414.

[51] Int. Cl.² .............................................. A61M 1/03
[52] U.S. Cl. ........................... 23/258.5 M; 128/DIG. 3
[58] Field of Search .................. 23/258.5 A, 258.5 M, 23/258.5 MH; 128/DIG. 3; 210/321 B

[56] References Cited

U.S. PATENT DOCUMENTS

| 3,070,092 | 12/1962 | Wild et al. | 23/258.5 A |
| 3,396,849 | 8/1968 | Lande et al. | 23/258.5 MH X |
| 3,413,095 | 11/1968 | Bramson | 23/258.5 M |
| 3,480,401 | 11/1969 | Holm et al. | 23/258.5 M |
| 3,484,211 | 12/1969 | Mon et al. | 23/258.5 MH |
| 3,506,406 | 4/1970 | Birch | 23/258.5 M |
| 3,541,595 | 11/1970 | Edwards | 23/258.5 M X |
| 3,547,271 | 12/1970 | Edwards | 23/258.5 M X |
| 3,612,281 | 10/1971 | Leonard | 23/258.5 M X |

FOREIGN PATENT DOCUMENTS

| 1,568,130 | 5/1969 | France | 23/258.5 M |
| 1,597,874 | 8/1970 | France | 23/258.5 M |

OTHER PUBLICATIONS

Crescenzi et al., "A Pulsatile Extracorporeal Membrane System", San Diego Symposium for Biomed. Eng., 1963, pp. 27-31.

Primary Examiner—Barry S. Richman
Attorney, Agent, or Firm—Paul C. Flattery; Garrettson Ellis

[57] ABSTRACT

An oxygenator for blood which comprises means for removably holding a membrane oxygenator unit, means for conveying blood to a patient through the oxygenator unit in a first flow path and back to the patient, and means for supplying oxygen gas through the oxygenator unit in a second flow path separated from the first flow path in the unit by a semi-permeable membrane. The oxygenator unit holding means carries a plate which has an oxygen inlet manifold port positioned to communicate with a mounted oxygenated unit, to provide a sealed oxygen flow path through the plate into the oxygenator unit and to provide for dispersal of effluent oxygen in a plurality of directions, thereby preventing the accidental obstruction of the oxygen outlet of the unit.

6 Claims, 5 Drawing Figures

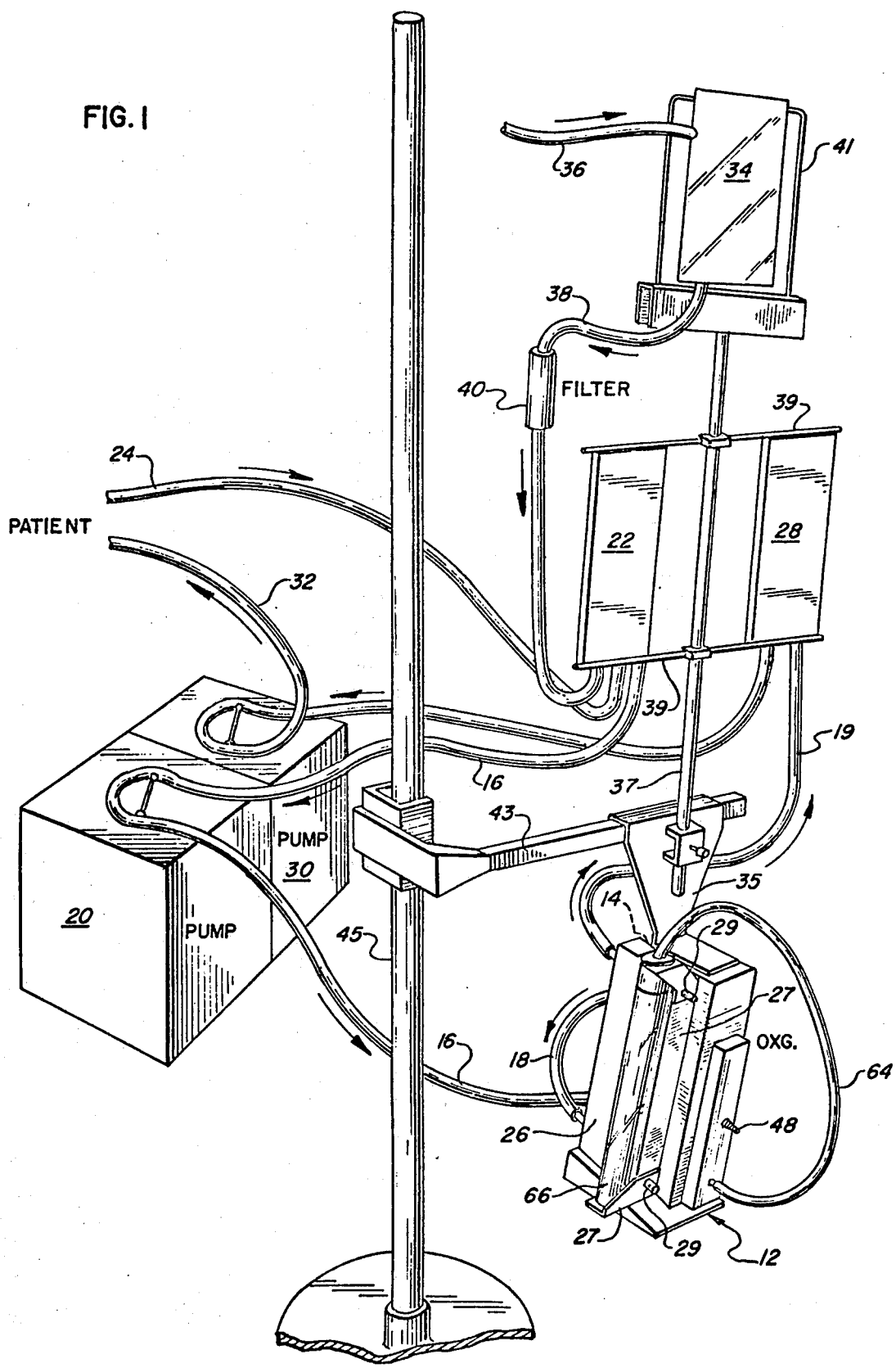

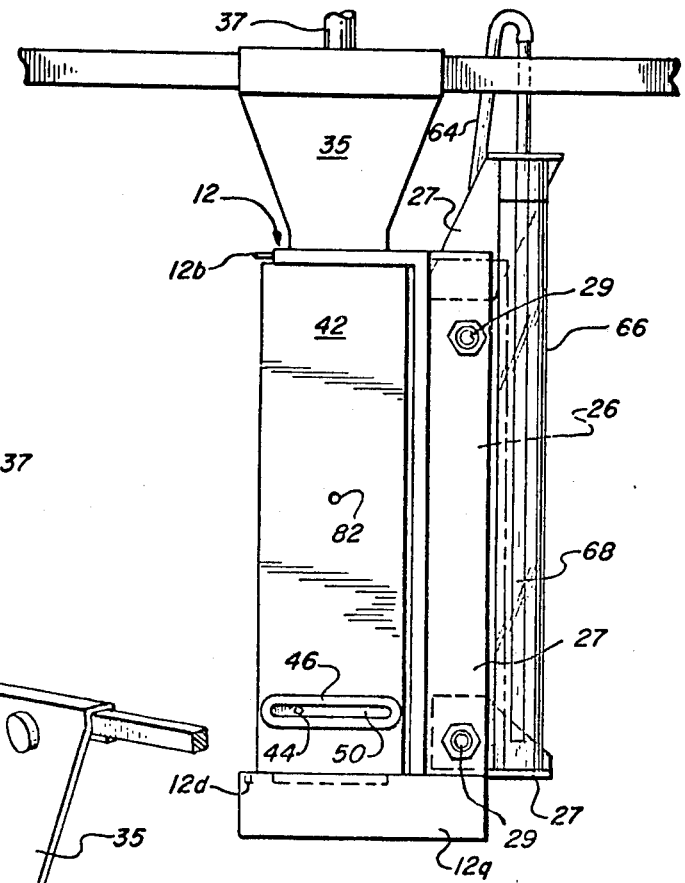
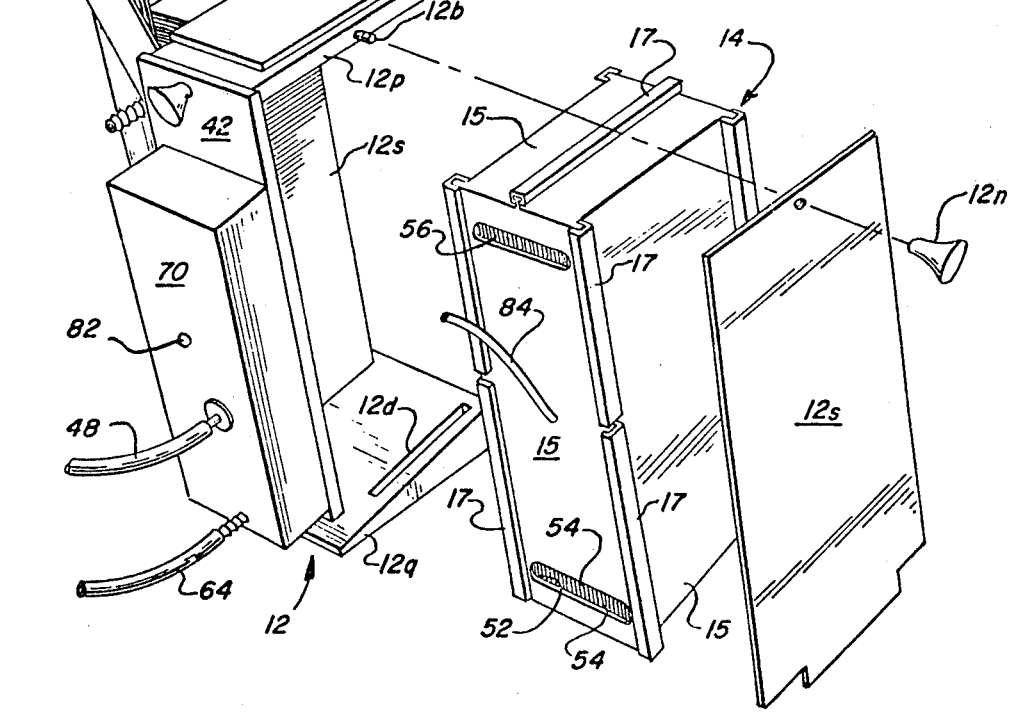

BLOOD OXYGENATOR UTILIZING A REMOVABLE MEMBRANE OXYGENATOR UNIT

This is a continuation of application Ser. No. 622,184, filed Oct. 14, 1975, and now abandoned, which is, in turn, a division of application Ser. No. 435,143 filed Jan. 14, 1974 and now U.S. Pat. No. 3,929,414, issued Dec. 30, 1975.

BACKGROUND OF THE INVENTION

Membrane oxygenators for blood are attracting growing medical interest because of their capability of partially or completely taking over the respiratory function of a patient for a period of many hours and even days without unacceptable damage to the blood supply. Previously, bubble-type oxygenators involving the direct application of oxygen bubbles through a stream of blood had been used in open heart surgery for periods up to four or five hours. However, unacceptable damage frequently is inflicted upon the blood supply of the patient if the bubble oxygenators remain in operation for periods significantly longer than this.

Commercially available disposable membrane oxygenator units are disclosed in U.S. Pat. No. 3,757,955. The same patent describes a membrane oxygenator unit currently under development in which the membrane is made of a porous, hydrophobic material such as 3 or 4 mil polytetrafluoroethylene sheeting having an effective pore diameter of about 0.5 micron. Such materials are capable of rapidly transferring oxygen, carbon dioxide and water vapor, while preventing the transfer of blood itself through the membrane. Porous membrane oxygenator units exhibit an oxygen and carbon dioxide transfer capability which greatly exceeds the older membrane oxygenator unit designs which utilize thin silicone rubber membrane and the like. Accordingly, porous membrane oxygenator units can support the total respiratory needs of a patient with a significantly smaller total surface area of membrane than a conventional silicone rubber membrane oxygenator unit of similar design. As a result of this, the amount of blood which is removed from the body at any one time can be typically less with porous membrane oxygenator units, which is a significant and important advantage.

There is, however, a drawback to porous membrane oxygenator units: it is absolutely necessary for the pressure on the blood side of the membrane to at all times equal or exceed the pressure on the gas side of the membrane. If these conditions fail, the increased gas pressure may drive gas bubbles through the membrane into the blood flow path, from where the gas bubbles may be conveyed back to the patient. This could create a life-threatening embolism in the patient.

Accordingly, in U.S. patent application Ser. No. 390,567 filed Aug. 22, 1973 by Ronald J. Leonard, an oxygenator apparatus is provided for the safe and effective utilization of hydrophobic, porous membrane blood oxygenator units. In the device described in the patent application, a manometer means is provided to assure safe and reliable limitation of the gas pressure in the oxygenator unit.

Also, the aforesaid application discloses heat exchanging means and the like for maintaining the appropriate blood temperature and other desirable parameters of operation.

For the commercial manufacturer of porous membrane blood oxygenator units, it is a matter of great importance to be certain that the customers utilize the oxygenator unit in a correct manner, using the correct equipment for mounting and supplying blood and oxygen to the membrane oxygenator unit, so that there will be no dangerous gas overpressure, driving oxygen bubbles into the blood path, which can instantly create a life-threatening situation.

In accordance with this invention, an oxygenator and membrane oxygenator unit for use therein are provided in which the membrane oxygenator unit is used only with great difficultly apart from the oxygenator itself, which can be designed to provide the necessary parameters of operation that result in safe use. Accordingly, a relative foolproof system is provided for the protection of patients.

Furthermore, in accordance with this invention, a system is provided for assured, unrestricted exhaust of gas, to prevent any obstruction of the flow of gas from the oxygenator unit, thus avoiding a consequent, potentially disastrous rise in the gas pressure of the oxygen flow path in the oxygenator unit.

DESCRIPTION OF THE INVENTION

The blood oxygenator of this invention comprises means for removably holding a membrane oxygenator unit, and means for conveying blood from a patient through the oxygenator unit in a first flow path and back to the patient. The oxygenator also has means for supplying oxygen gas through the oxygenator unit in a second flow path separate from the first flow path and separated from it in the oxygenator unit by a semipermeable membrane. In accordance with this invention, the means for holding the oxygenator unit is adapted to carry a plate in a position to engage an oxygenator unit installed in the holding means of the oxygenator. The plate defines an oxygen inlet manifold port positioned to communicate, while engaged with the oxygenator unit, with the inlet of the second flow path of the oxygenator unit, to provide a sealed oxygen flow path through the plate into the oxygenator unit.

As a result of this arrangement, oxygen comes to the plate by means of an oxygen line, and is manifolded or spread into a wide flow path for delivery to the individual oxygenator unit flow channels by means of parts carried by the oxygenator itself rather than the oxygenator unit. As a result of this, oxygenator units desired for use with the device of this invention do not carry an oxygen manifolding means, and thus are not conveniently used with makeshift equipment. Hence, the user of a disposable oxygenator unit is strongly encouraged to utilize the standard equipment for that unit with its tested safety features, rather than to inconveniently improvise his own arrangement of apparatus.

A typical membrane oxygenator unit defines blood and oxygen flow paths comprising a plurality of interleaving parallel channels. It is contemplated that the typical oxygenator units for use in accordance with this invention will have a wide mouth opening for inlet of oxygen and outlet of spent gases to and from the oxygenator unit, with the inlets and outlets of the parallel, interleaved oxygen channels in the oxygenator unit being directly exposed to the exterior of the unit through the wide mouth openings. The manifold port on the plate of the blood oxygenator is accordingly proportioned to surround and seal the wide mouth opening around the inlets of the parallel channels, to provide the sealed oxygen flow path. The wide mouth opening of the oxygen inlet to the membrane oxygenator unit prevents the simple attachment of an oxygen line to the oxygenator unit, and thus encourages the use of the standard oxygenator equipment especially manufactured for use with the membrane oxygenator unit, which will include the necessary safety features such as a means for limiting gas pressure, a heat exchange unit, and the like.

Furthermore, in position of use the plate, with the exception of the manifold port area, is spaced from the membrane oxygenator unit in a position to overlie the gas outlet port of the second flow path of the oxygenator unit. Accordingly, oxygen gas escapes through the outlet port, then passing in many directions of flow between the oxygenator unit and the plate to the exterior. The advantage of this is that such arrangement greatly reduce the possibility of some accidental obstruction of the gas outlet port, such as might take place if the outlet port were a simple tube or opening. The reason this is necessary is that the accidental placement of some obstructing object, even momentarily, in front of the gas outlet port during operation could cause a sudden rise of gas pressure within the membrane oxygenator unit, which is dangerous for reasons discussed above.

In the drawings:

FIG. 1 is a schematic view of an oxygenator of this invention, with a porous membrane oxygenator unit installed in the holding means.

FIG. 2 is a rear plan view of the oxygenator unit holding means of this invention, with one side wall of the holding means removed, without an oxygenator present, and with the heat exchanger means shown in phantom.

FIG. 3 is a perspective view of the oxygenator unit holding means of this invention with a side wall removed, showing a typical membrane oxygenator unit prior to installation in the oxygenator unit holding means.

Figure 4:
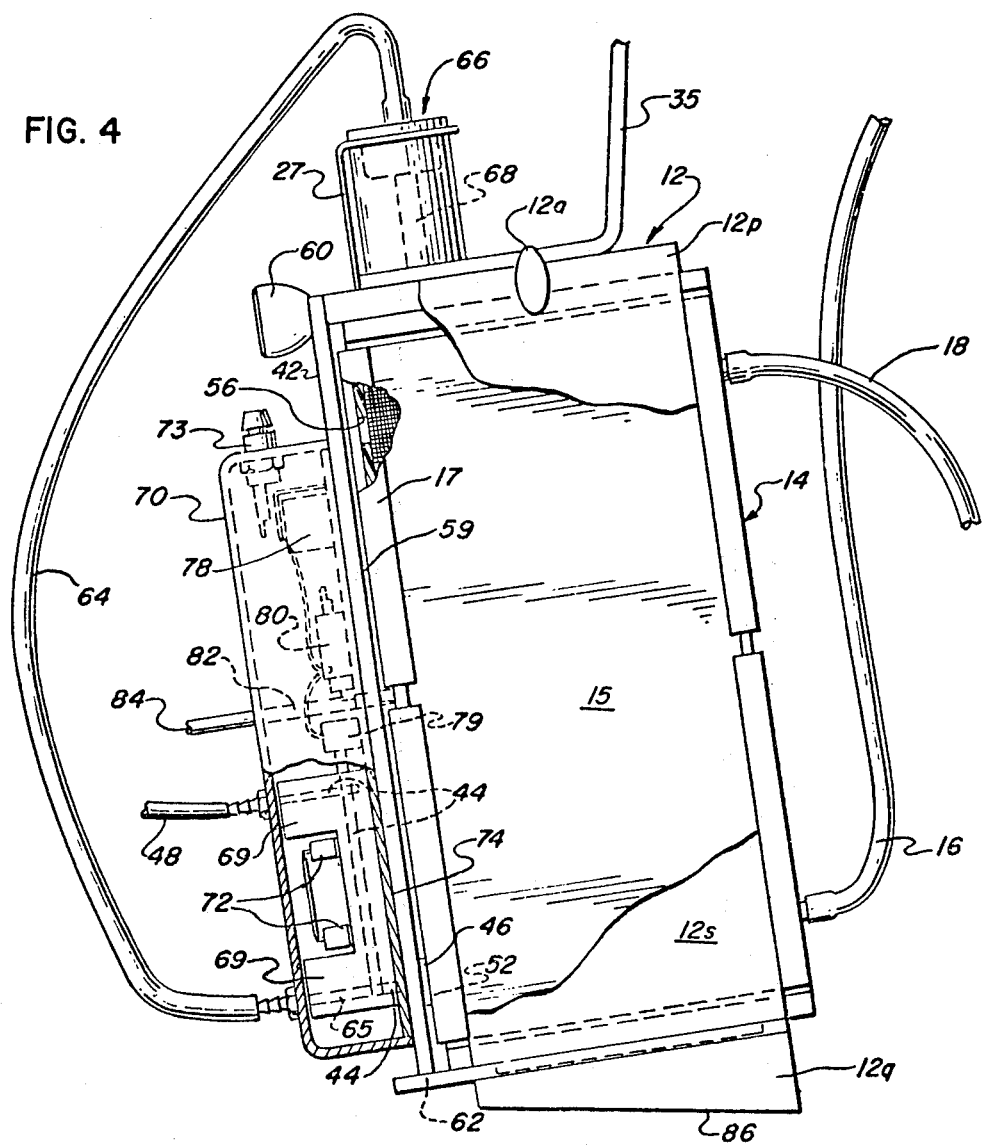
FIG. 4 is a side elevational view of the oxygenator unit holding means of this invention with the oxygenator unit installed, portions of the oxygenator unit and holding means being broken away and shown in section.

Referring to the drawings, an oxygenator is shown which comprises, means 12 for removably holding a membrane oxygenator unit 14. Means for conveying blood from a patient through the oxygenator in a first flow path and back to the patient are also provided. Blood in inlet tube 16 is propelled through the oxygenator by a conventional roller pump 20, being drawn out of the venous reservoir 22. Blood is supplied to the venous reservoir through conduit 24 from the patient's venous supply.

Downstream from the oxygenator, blood passes from the oxygenator into blood outlet tubing 18, and from there through heat exchanger 26 (such as disclosed in U.S. Pat. No. 3,640,340), to arterial reservoir 28 by tube 19, from where it is propelled by a second roller pump 30 into the patient's arterial blood supply through conduit 32. Heat exchanger 26 is mounted on bracket 27 with its heat exchange fluid flow path inlet and outlet in communication with ports 29, which pass through bracket 27 of holder 12 for connection with a heat exchange fluid source.

A cardiotomy reservoir 34 can be provided to receive blood from a cardiotomy sucker which sucks blood from the patient's incision site or the like, and passes it to the reservoir through line 36. The cardiotomy reservoir is connected by line 38 to a filter 40, which in turn connects with the venous reservoir 22.

Unit holding means 12 is held by bracket 35, which in turn carries a mast 37 having hangers 39, 41 for removably holding bood containing components of the oxygenator. Bracket 35 is in turn held on a hanger 43 which is attached to supporting member 45.

Referring also to FIGS. 2 through 5, details of oxygenator unit holder 12 and related parts are shown.

Holder 12 is shown to carry an oxygenator unit engaging plate 42, which in turn defines an oxygen inlet manifold port 44 which terminates at its inner end with an O-ring seal 46. A source of oxygen gas is provided through oxygen inlet line 48 to communicate with oxygen inlet manifold port 44, which provides a sealed oxygen flow path through the plate into the oxygenator unit.

Recessed portion 50 within O-ring 46 is provided to permit the oxygen gas to freely flow throughout the entire interior of O-ring seal 46.

Figure 5:
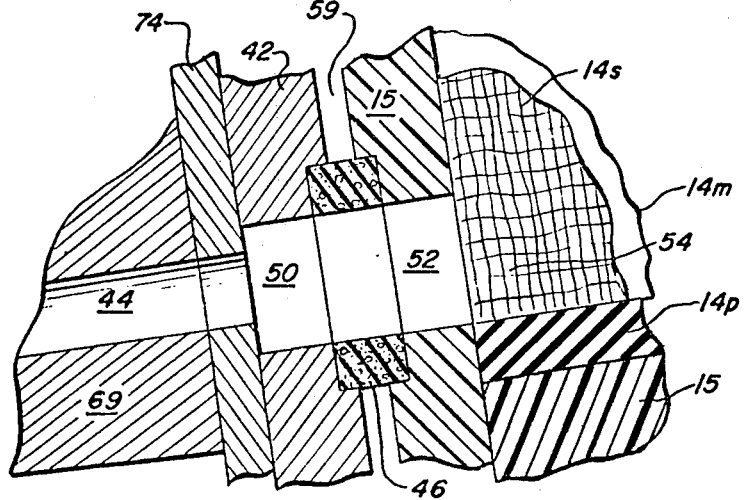
FIG. 5 is an enlarged view in vertical section of the vicinity of the oxygen inlet of the oxygenator unit as shown in FIG. 4.

Inlet manifold port 44, O-ring seal 46, and recessed portion 50 are positioned to communicate in sealing relation with the oxygen inlet 52 of oxygenator unit 14 as shown in FIGS. 3 and 5. As can be seen from FIG. 3, oxygen inlet 52 is elongated so that the many inlet ends of parallel flow channels 54 of conventional oxygenators are all directly exposed to the exterior of the oxygenator unit through inlet 52. O-ring seal 46, as part of the manifold port of plate 42, is proportioned to surround and seal inlet 52 of oxygenator unit 14 to provide a sealed oxygen flow path when unit 14 is installed in holder 12.

Oxygen flow path outlet port 56 of unit 14 is also typically elongated to permit the free exit of surplus oxygen gas, plus carbon dioxide and water vapor which is passed into the second flow path of oxygenator unit 14.

In FIG. 5, a typical construction of the layers which define flow paths 54 is shown. Porous, semi-permeable membrane 14H overlies support screening 14S is a convoluted, multilayer arrangement as further illustrated in U.S. Pat. No. 3,757,955. The edges of the membrane and screening are sealed together by a line of cured potting compound 14P, and the structure is encased between walls 15, which are held together by fasteners 17 (FIG. 3).

As shown in FIG. 4, oxygenator unit engaging plate 42 is positioned to be spaced from and define an unbroken wall 58 over gas outlet port 56 of the oxygenator unit in position of use and separated by space 59, which is typically about 1/8 inch wide. As a result of this, exhaust gas from outlet 56 has unrestricted exit in a plurality of directions through space 59 between plate 42 and unit 14. The result of this is to greatly reduce the probability of accidental obstruction of outlet 56, since gas will vent adequately from oxygenator unit 14 as long as any substantial portion of elongated space 59 remains open to the exterior.

Plate 42 is attached to holder 12 by a removable nut 60 at one end and conventional detent means 62 at its other end, so that plate 42 is easily removable from holder 12.

Line 64 and conduit 65 through cover 70 provide communication between the oxygen inlet manifold port 44 and safety means 66, held by bracket 27, for preventing the pressure of oxygen gas in the inlet manifold port from reaching a level sufficient to cause gas bubbles to pass through the porous, semipermeable membrane 14m of oxygenator unit 14. This safety means 66 comprises a liquid-filled tube having a rigid, tubular extension 68 of line 64, which safety means functions as a pressure limiting device in the manner described in U.S. Pat. application Ser. No. 390,567, filed Aug. 22, 1973 by Ronald J. Leonard and now U.S. Pat. No. 3,927,980 issued Dec. 23, 1975.

Oxygenator unit holder 12 also comprises top and bottom plates 12p, 12q, and side walls 12s, which are secured together in the manner previously described for plate 42, by means of nuts 12n which fit on bolts 12b, and detent means 12d. Plate 12p is attached by glueing or welding to bracket 35. Oxygenator unit 14 is optionally not enclosed along its rear, blood flow side.

In the specific embodiment shown herein, inlet manifold port 44 does not pass straight through plate 42, bt makes two right angle turns as shown in FIG. 4 so as to pass through a U-shaped heater block 69 which is mounted within cover 70 which, in turn, is carried by plate 42. Heater block 69, through which inlet manifold port 44 passes as an elongated channel, provides means to warm the oxygen gas entering into the oxygenator unit to a predetermined temperature. A typical heater block 69 usable herein can be a typical 45 watt, 120 volt, 3-ohm electric cartridge heater. Conduit 65 also passes through heater block 69 to communicate with manifold port 44 therein.

Heater block 69 is controlled by two thermostats 72, electrically connected together so that the disconnection of either thermostat deactivates heater block 69. The purpose of this is to provide a high degree of assurance that the oxygen gas is not overheated, since oxygen gas temperatures in excess of 42° C. could cause serious damage to blood in the oxygenator. Fuse 73 is also provided for added safety.

Insulating wall 74 prevents undue heat loss from heater block 69. If desired, an alarm means can be provided to activate alarm buzzer 78 when a pressure switch 79 mounted in fluid communication with the inlet manifold port 44 is not sensing a gas pressure in excess of a standard pressure of at least 6 inches of water, which is equivalent to approximately 5 liters per minute of oxygen flow through port 44 when the port diameter is about one-fourth inch. This arrangement may comprise a conventional relay 80 activating buzzer 78 when the predetermined gas overpressure is not sensed.

Port 82 is defined completely through plate 42 and cover 70 to permit the passage of inflation line 84 of oxygenator unit 14 therethrough. Inflation line 84 communicates with an inflatable shim inside of oxygenator 14 which can be used to pressurize the screening layers 14s and membrane layers 14m together to counter-balance the tendency of the oxygenator unit to expand due to the blood pressure pushing the screening and membranes apart.

The inflatable shim may be placed at the midpoint of the stack of screening and membrane layers, or it can be of U-shaped cross-sectional construction to provide a pair of expansion members on each side of the stack for the same purpose. Other designs of inflatable shim can also be used.

Typically, unit holder 12 is positioned at an angular relationship to the vertical by bracket 35, to elevate the blood outlet as shown in FIG. 4, to facilitate the priming of the oxygenator unit with blood or saline solution. The angular relationship facilitates the removal of all air bubbles from the oxygenator unit into outlet line 18 during priming. Bottom plate 12q has a beveled lower edge 86 so that unit holder 12 assumes the same angular relationship to the vertical when resting on a horizontal surface, before being hung by bracket 35 on arm 43. Thus, unit holder 12 can be conveniently loaded with an oxygenator unit, and the unit primed with saline solution, prior to hanging on arm 43.

The above has been offered for illustrative purposes only, and is not intended to limit the invention of this application which is as described in the claims below.

What is claimed is:

1. A blood oxygenator defining a blood flow path and an oxygen flow path in a manner which allows the blood flowing therethrough to be oxygenated comprising: a membrane defining an interface between the oxygen flow path and the blood flow path; a housing for holding said membrane, said housing defining said blood flow path on one side of the membrane and the oxygen flow path on the other side of the membrane, said blood and oxygen flow paths being sealed from one another, said housing defining inlets and outlets for each of said oxygen and said blood flow paths; a bracket means for removably engaging and holding said housing in a predetermined disposition, said bracket means further comprising a means for at least partially shielding said oxygen outlet from external obstruction and for dispersing oxygen passing from the oxygen outlet of said housing into a plurality of directions to prevent accidental obstruction of said outlet.

2. A blood oxygenator of claim 1 wherein said means for dispersing the oxygen in a plurality of directions includes a wall member positioned substantially normally to the flow path defined by said oxygen outlet, said wall member being spaced from said oxygen outlet whereby the oxygen impinging on the wall member is diverted into said plurality of directions.

3. The blood oxygenator of claim 2 wherein said bracket means includes a bracket oxygen flow path therethrough and engagement means at one end of said bracket oxygen flow path for sealingly engaging said oxygen inlet of said housing to allow oxygen to flow through the bracket means and into the housing.

4. In a blood oxygenator which comprises bracket means removably holding membrane means for the oxygenation of blood, said membrane means having separate blood and oxygen inlets and outlets, the improvement comprising, in combination: plate means engaging said membrane means, said plate means being selectively removable from engagement with said membrane means, said plate means including means defining an oxygen inlet manifold port positioned to communicate with the oxygen inlet of said membrane means when said plate means is engaged therewith, and means providing a sealed, oxygen flow path through said manifold port means into said membrane means when said plate means is engaged therewith, said plate means being positioned to be spaced from and to define an unbroken wall over the oxygen outlet of said membrane means, whereby exhaust gas from said oxygen outlet has unrestricted exit in a plurality of directions between said plate means and said membrane means when in engaged relationship, to prevent accidental obstruction of said outlet.

5. The blood oxygenator of claim 4, the improvement further comprising said means to provide a sealed, oxygen flow path comprising an O-ring seal carried by said plate means about said manifold port means, and positioned to sealingly engage the oxygen inlet of said membrane means.

6. The oxygenator of claim 5, the improvement further comprising said membrane means being disposed in angular relationship to the vertical to elevate the blood outlet above the gas outlet and the blood and gas inlets, to facilitate gas bubble removal from said blood outlet.

* * * * *